United States Patent [19]

Yamaguchi

[11] Patent Number: 4,904,256

[45] Date of Patent: Feb. 27, 1990

[54] MAGNETIC ARTIFICIAL ANUS HAVING SPHINCTER FUNCTION

[75] Inventor: Takashi Yamaguchi, Hamamatsu, Japan

[73] Assignee: Meito Sangyo Kabushiki Kaisha, Aichi, Japan

[21] Appl. No.: 130,382

[22] PCT Filed: Feb. 24, 1987

[86] PCT No.: PCT/JP87/00119

§ 371 Date: Oct. 20, 1987

§ 102(e) Date: Oct. 20, 1987

[87] PCT Pub. No.: WO87/04917

PCT Pub. Date: Aug. 27, 1987

[30] Foreign Application Priority Data

Feb. 24, 1986 [JP] Japan .................................. 61-37448

[51] Int. Cl.⁴ ............................ A61F 2/48; A61F 2/51

[52] U.S. Cl. ............................... 623/14; 428/DIG. 25

[58] Field of Search ................... 623/3, 10, 11, 12, 14, 623/66; 128/1 R, DIG. 25; 335/303

[56] References Cited

U.S. PATENT DOCUMENTS 4,209,010  6/1980  Ward et al. .................. 128/DIG. 25
4,210,132  7/1980  Perlin ........................... 128/DIG. 25

Primary Examiner—Richard J. Apley
Assistant Examiner—David J. Isabella
Attorney, Agent, or Firm—Wenderoth, Lind & Ponack

[57] ABSTRACT

A magnetic artificial anus assembly comprising a combination of an annular bag structure formed of a bio-affinitive flexible material and filled with a magnetic fluid and a plug structure having a magnet member. It has a sphinter function similar to the natural anus.

5 Claims, 2 Drawing Sheets

MAGNETIC ARTIFICIAL ANUS HAVING SPHINCTER FUNCTION

TECHNOLOGICAL FIELD

This invention relates to a new type of magnetic artificial anus which can newly impart constricting function, to artificial anuses constructed in a condition devoid of a sphincter function and can overcome the defects and disadvantages of conventional artificial anuses.

BACKGROUND TECHNOLOGY

When the anus is removed because of colon cancer, rectum cancer or metastasis of a malignant tumor in the placenta to the rectum or for some other reason, it is the practice to build a single-hole artificial anus in the abdominal wall by using the transverse colon, descending colon or sigmoid colon. Such an artificial anus does not have a sphincter function.

The number of patients devoid of constricting function has increased year by year with the increasing number of aged people or increasing cases of cancer of the large intestine. At present, however, there is substantially no medically effective means of reviving the sphincter function, and it has been strongly desired to develop a practical method of artificially reviving the constricting function.

As measures for preventing leakage of feces from the artificial anus, it has been the previous practice to apply a closure or stopper made of gauze or other suitable materials to the opening part of the artificial anus, or to attach a LAPAC (a bag having a rim for bonding in the edge portion of its opening) to the skin around the opening part of the artificial anus using an adhesive. Such measures, however, cause various troubles unbearable to the patients, such as the occurrence of contact dermatitis owing to the adhesive or the occurrence of malodors from feces that might be leaked.

In an attempt to overcome such troubles, a magnet-type artificial anus was proposed. For example, "Shujutsu" (Operation), vol. 33 (1979), pages 369–373 describes a magnetic artificial anus shown by the longitudinal sectional view of FIG. 5 attached to the present application (hatches showing the cut section are partly omitted). As shown in FIG. 5, the conventional magnetic artificial anus has a ring-like permanent magnet 30 implanted between a subcutaneous tissue 5 and a muscular tissue so as to surround the periphery of an artificial anus wall 3. The opening of the artificial anus is plugged by a stopper member 33 having a leg portion 2" capable of being inserted into the opening portion of the artificial anus, a magnet cap 31 and a filter washer 32 embedded in the cap. The stopper member 33 is held and fixed in position by utilizing the magnetic attracting force between the ring-like permanent magnet 30 and the magnet cap 31.

Since in such a conventional magnet-type artificial anus, the heavy ring-like permanent magnet is implanted in the tissues, the magnet descends by gravity and unduly causes bending of the colon, or the skin tissues between the ring-like permanent magnet and the stopper member are pressed and necrotized. Furthermore, the patient has a strong feel of having a foreign object present. Hence, this conventional artificial anus is no longer used now in practice.

It is an object of this invention therefore to provide an artificial anus which can overcome the technical problems of the conventional magnetic artificial anus.

DISCLOSURE OF THE INVENTION

The present inventors hit upon an idea of overcoming the aforesaid technical problem by utilizing a magnetic fluid capable of being magnetized, and have made investigations thereinto.

These investigations have led to the discovery that by embedding an annular bag structure formed of a bio-affinitive flexible material such as silicone rubber and filled with a magnetic fluid in the subcutaneous tissue or muscular tissue so as to surround the periphery of an artificial anus wall, and plugging it with a plug structure having a leg portion capable of being inserted into the opening portion of the artificial anus, that part of the leg portion which faces the annular bag structure via the artificial anus wall being formed of a magnet member sphincter function close to a natural physiological condition which is in the direction from the periphery of the section of the artificial anus wall to its center, which is the same as the sphincter direction of a natural anus, can be imparted to the artificial anus, and the artificial anus is free from undue bending of the colon due to descending of the artificial anus, and pressing and necrosis of skin tissues between the ring-like permanent magnet and the stopper in the conventional artificial anus, and the strong feel of having a foreign object present.

It has further been found that many other improvements can be obtained. For example, since the annular bag structure filled with a magnetic fluid can be deformed by adapting well to motions of the body (twisting, pressing, etc.), trouble with the artificial anus can be avoided. There is no occurrence of contact dermatitis or malodors as in the case of using a conventional LAPAC. Furthermore, the patient need not to be afraid of trouble owing to leakage of feces during bathing or outdoor activities. In addition, because of the structure of the artificial anus in accordance with this invention, there is no likelihood of complications such as proctoptosis, hernia and stenosis which sometimes occur in conventional artificial anuses.

Thus, the present invention provides a magnetic artificial anus having a sphincter function comprising a combination of an annular bag structure filled with a magnetic fluid and formed of a bio-affinitive flexible material, said bag structure being embedded in a subcutaneous tissue or a muscular tissue so as to surround the periphery of an artificial anus wall, and a plug structure having a leg portion capable of being inserted into the opening portion of the artificial anus, at least that part of the leg portion which faces the annular bag structure via said wall being formed of a magnet member.

Figure 1:
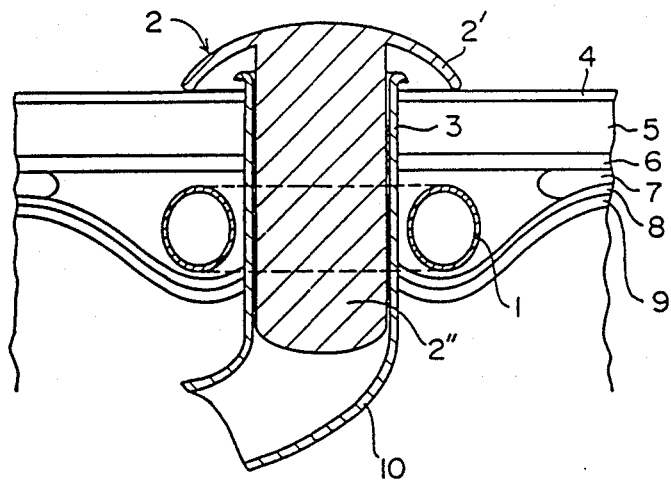
FIG. 1 is a longitudinal sectional view (hatches showing the section are partly omitted) showing one example of the magnetic artificial anus of this invention.

In the accompanying drawings, the reference numerals show the following members.

1, annular bag structure; 2, plug structure; 2', the cap of the plug structure; 2", the leg portion of the plug structure; 3, the wall of the artificial anus; 4, skin; 5, subcutaneous tissue; 6, the outer fascia of the abdominal wall; 7, abdominal muscles; 8, the inner fascia of the abdominal wall; 9, peritoneum; 10, colon; 11, handle; 12, ring-like permanent magnet; 13, adhesive; 14, ventilation hole; 15, gas permeation filter; 16, filling material; 17, film; 18, cylindrical permanent magnet; 30, ring-like permanent magnet; 31, magnet cap; 32, filter washer; 33, stopper member.

BEST MODE OF PRACTICING THE INVENTION

For details of the present invention, the magnetic artificial anus of this invention having a sphincter function near that in a natural physiological condition will be described with reference to the accompanying drawings.

Figure 2:
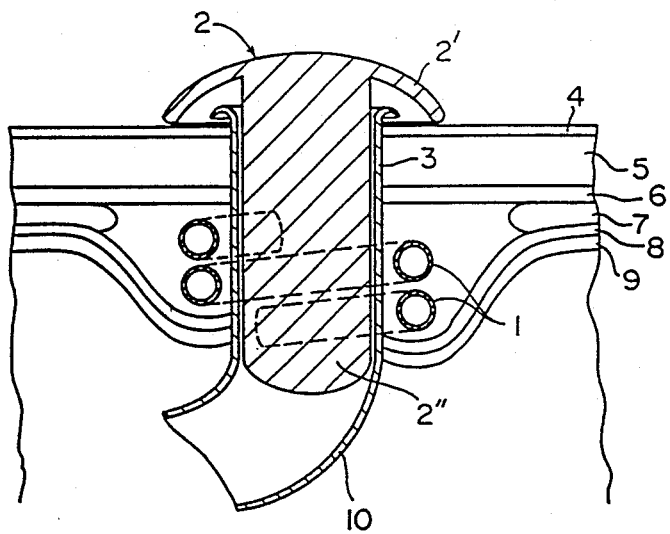
FIG. 2 is a similar longitudinal section showing another example of the magnetic artificial anus of this invention.

As shown in FIGS. 1 and 2, the magnetic artificial anus of this invention comprises a combination of an annular bag structure 1 filled with a magnetic fluid and formed of a bio-affinitive flexible material for embedding in a suitable part of a subcutaneous tissue 5 or a muscular tissue [outer fascia 6, abdominal muscles 7, inner facsia 8] and between the fascia 8 and the fascia 9 so as to surround the periphery of the artificial anus wall 3, and a plug structure 2 having a leg portion 2" capable of being inserted into the opening portion of the artificial anus, that part of the leg portion 2" which faces the annular bag structure 1 via the artificial anus wall 3 being formed of a magnet member.

The annular bag structure is formed of a bioaffinitive flexible material. Materials having moderate flexibility and strength and bio-affinity may be properly selected from various materials used in artificial organs, and used as the bio-affinitive flexible material. Examples of such materials are natural and synthetic rubbers, and proper blends thereof. Examples of the synthetic rubbers include isoprene rubber, ethylene/propylene rubber, acrylic elastomers, propylene oxide rubber, polyether rubber, chloroprene rubber, butadiene rubber, styrene/butadiene rubber, silicone rubbers and urethane rubbers.

The annular bag structure may be of any annular shape capable of being embedded in the subcutaneous or muscular tissue so as to surround the periphery of the wall of the artificial anus, such as a doughnut-shape shown in FIG. 1 or a helical hollow structure shown in FIG. 2. The inside diameter of the annular bag structure 1 may be properly varied depending upon the size of the colon of the patient, his body type, etc. Preferably, it is nearly equal to the outside diameter of the artificial anus wall. The sectional shape and size of the annular bag structure can also be properly changed. Its sectional shape is preferably a circular to elliptical sectional shape, and the outside diameter of its section is properly selected within the range of, for example, about 5 to about 15 mm. The film thickness of the bag structure can be selected and changed depending upon the material from which the bio-affinitive flexible material is made, the desired amount of the magnetic fluid to be filled, etc. For example, the film thickness is about 0.1 to about 0.5 mm, preferably about 0.1 to about 0.2 mm.

In the present invention, the annular bag structure 1 described above is filled with a magnetic fluid. Such a magnetic fluid preferably has a low specific gravity, a high susceptibility and good stability with time and is non-toxic to the living body. Examples of such a magnetic fluid are the aqueous sol of magnetic iron oxide-dextran complex disclosed in Japanese Patent Publication No. 13521/1984 (corresponding to U.S. Pat. No. 4,101,435), the magnetic fluid containing water as a dipersing medium disclosed in Japanese Patent Publication No. 40069/1979, (a magnetic fluid is obtained by adding a surfactant based on an unsaturated fatty acid or its salt to an aqueous suspension of a wet-process ferromagnetic oxide powder in an amount more than sufficient to form a unimolecular film on the surface of the oxide particles, lowering the pH below 7 to flocculate the suspended particles, washing the flocculate with water or some other polar solvent, then dispersing the solid in an aqueous medium containing an anionic or nonionic surfactant) and the magnetic fluid containing an oil as a dispersing medium disclosed in Japanese Patent Publication No. 17118/1978 (magnetic fluids are obtained by suspending fine powders of a wet-process ferromagnetic oxide in water, adding a surfactant based on a fatty acid or its salt to the suspension in an amount more than sufficient to form a unimolecular film on the oxide particles, flocculating the dispersed particles by lowering the pH to less than 7, washing the flocculate with water or a polar solvent, dewatering, then dispersing the solid in oil). Among them, the aqueous sol of magnetic iron oxide-dextran complex disclosed in Japanese Patent Publication No. 13521/1984 is preferred. The amount of the magnetic fluid to be filled is limited by the inner capacity of the annular bag structure. For example, it may be about 5 to about 30 ml.

The magnetic artificial anus of this invention is composed of a combination of the magnetic fluid-filled annular bag structure 1 described above, and the plug structure 2 having the leg portion 2" capable of being inserted into the opening portion of the artificial anus, at least that part of the leg portion which faces the annular bag structure 1 via the artificial anus wall 3 being formed of a magnet member.

Examples of the magnet member include permanent magnets such as an alnico magnet described in JISC 2502, 1966, rare earth-cobalt magnets such as a samarium cobalt magnet ($SmCo_5$) described in Appl. Phys. Letters, 17, 176 (1970), a neodymium-iron-boron magnet described in J. Appl. Phys., 55, 2083 (1984), a barium ferrite magnet, and a strontium ferrite magnet described in J. Appl. Phys., 40, 1294 (1969). The neodymium-iron-boron magnet and the samarium cobalt magnet are preferably used because they have a strong magnetic force and make the plug structure 2 lighter in weight.

The above-mentioned alnico magnet as described in JISC 2502 has the following magnetic characteristics:

| Classification | | Symbol | Residual magnetic flux density Br | | Coercive force Hc | | Maximum energy product (BH) max | | Reference Recoil permeability $\mu_{rec}$ | Density D |
|---|---|---|---|---|---|---|---|---|---|---|
| | | | T | kG | kA/m | Oe | kJ/m³ | MG.Oe | G/Oe | g/cm³ |
| Class 2 | A | MCA 140 | 0.55~0.70 | 5.5~7.0 | 41.4~49.4 | 520~620 | 9.5~11.9 | 1.2~1.5 | 3~5 | 7.0 |
| | | MCA 160 | 0.06~0.73 | 6.0~7.3 | 49.4~57.3 | 620~720 | 11.9~13.5 | 1.5~1.7 | 3.5~5 | 7.3 |
| | | MCA 230 | 0.56~0.66 | 5.6~6.6 | 79.6~87.6 | 1000~1100 | 15.9~19.9 | 2.0~2.5 | 3~4 | 7.3 |
| | | MCB 360 | 0.95~1.05 | 9.5~10.5 | 55.7~60.5 | 700~760 | 25.5~31.8 | 3.2~4.0 | 4~5 | 7.3 |
| | | MCB 420 | 1.15~1.25 | 11.5~12.5 | 49.4~54.1 | 620~680 | 28.6~38.2 | 3.6~4.8 | 4~5 | 7.3 |
| | | MCB 500 | 1.23~1.33 | 12.3~13.3 | 46.2~52.5 | 580~660 | 35.8~43.8 | 4.5~5.5 | 2.5~3.5 | 7.3 |
| | B | MCB 580 | 1.25~1.35 | 12.5~13.5 | 50.2~58.1 | 630~730 | 42.2~50.1 | 5.3~6.3 | 2.5~3.5 | 7.3 |
| | | MCB 750 | 1.30~1.40 | 13.0~14.0 | 54.1~59.7 | 680~750 | 53.3~65.3 | 6.7~8.2 | 1.5~2.5 | 7.3 |
| | | MCB 400 II | 0.80~0.90 | 8.0~9.0 | 95.5~111.5 | 1200~1400 | 27.9~35.8 | 3.5~4.5 | 2~3 | 7.3 |
| | | MCB 500 II | 0.85~0.95 | 8.5~9.5 | 107.5~119.4 | 1350~1500 | 35.8~43.8 | 4.5~5.5 | 2~3 | 7.3 |
| Class 3 | A | MPA 100 | 0.20~0.23 | 2.0~2.3 | 127.4~151.3 | 1600~1900 | 6.4~8.7 | 0.8~1.1 | 1.2 | 4.8 |
| | | MPB 280 | 0.33~0.36 | 3.3~3.6 | 159.2~207.0 | 2000~2600 | 19.9~23.9 | 2.5~3.0 | 1.1 | 4.8 |
| | | MPB 320 | 0.36~0.40 | 3.6~4.0 | 135.4~159.2 | 1700~2000 | 22.3~27.9 | 2.8~3.5 | 1.1 | 4.9 |
| | B | MPB 330 | 0.36~0.40 | 3.6~4.0 | 183.1~207.0 | 2300~2600 | 23.9~28.6 | 3.0~3.6 | 1.1 | 4.9 |
| | | MPB 380 | 0.40~0.43 | 4.0~4.3 | 143.3~175.2 | 1800~2200 | 27.9~31.8 | 3.5~4.0 | 1.1 | 5.0 |
| | | MPB 270 II | 0.32~0.36 | 3.2~3.6 | 207.0~238.9 | 2600~3000 | 18.3~23.9 | 2.3~3.0 | 1.1 | 4.8 |
| | | MPB 330 II | 0.36~0.40 | 3.6~4.0 | 238.9~270.7 | 3000~3400 | 23.9~28.6 | 3.0~3.6 | 1.1 | 4.9 |

The above-mentioned samarium cobalt magnet can be prepared as follows:

A melt of essentially $Co_5Sm$ is prepared by induction melting. This is crushed to coarse powder in a mortar and pestle. It is then further reduced to an average particle diameter of 6–8 μ by processing in a fluid energy mill using nitrogen as the working gas. A second melt of Co+60 wt % Sm is processed in a similar manner. This composition is selected as one of a series of compositions that would have a liquid-phase component at the sintering temperature of 1100° C. Samples for chemical analysis indicate 66.7% Co for the first powder and 40% Co for the second. The two powders are blended by tumbling to an average composition of 62.6% Co. This composition is in the range which produces maximum densification during sintering as disclosed by Cech [R. E. Cech (unpublished); also FIG. 44 in J. J. Becker, R. E. Cech, and D. L. Martin, Technical Report AFML-TR-70-76, Air Force Materials Laboratory, April 1970 (unpublished)]. Portions of this powder are placed in rubber tubes ⅜ in. (0.98 cm) in diameter and 1¾ in. (4.45 cm) long and packed to a density of 3.5 g/cc. These tubes of powder are placed in an axial magnetic field of 60,000–100,000 Oe in order to align the powder. After aligning, the rubber tubes are evacuated and then the samples are subsequently hydrostatically pressed to 200,000 psi. The pressed density is approximately 6.9 g/cc. The resultant bars are then ground to cylinders ¼ in. (0.64 cm) in diameter by 1¼ in. (3.18 cm) long. Subsequent sintering for ½ h at 1100° in high-purity argon increases the density to approximately 7.7 g/cc. Metallographic examination of the sintered bars shows approximately 10% void volume. These voids are of the noninterconnecting type.

The above-mentioned neodymium-iron-boron magnet can be prepared as follows:

Induction melts of the nominal compositions $Nd_xB_yFe_{100-x-y}$ with x=13~19 and y=4~17 are made in an alumina crucible under an argon gas atmosphere. The ingots are crushed in a nitrogen atmosphere to a particle size ~1 mm by a jaw crusher, to ~100 μm by a disk mill, and then, pulverized in 1,1,2-trichloro-1,2,2-trifluoroethane to about 3 μm by a ballmill with a stainless steel container and balls. The powders are aligned in a magnetic field of 800 kA/m and pressed perpendicular to the aligned direction at a pressure of 200 MPa. The green compacts are sintered in an argon gas atmosphere at temperature from 1310–1430 K for 1 h and then, cooled rapidly in a cooling chamber. The sintered samples are given a post-sintering heat treatment for 1 h at 400°~1400° K. and cooled rapidly.

The above-mentioned barium ferrite magnet and strontium ferrite magnet can be prepared as follows:

Single crystals of $BaFe_{12}O_{19}$ are grown from a $Na_2O$ flux with the method described by Gambino and Leonhard [R. J. Gambino and F. W. Leonhard, J. Am. Ceram. Soc. 44, 271 (1962)]. $SrFe_{12}O_{19}$ can also be grown by the same process. Single crystallinity is ascertained by the Laué back-reflection method of X-ray analysis with copper radiation. The densities, as determined by the pycnometer method, are 5.04 and 5.27 gm/cc for the $SrFe_{12}O_{19}$ and $BaFe_{12}O_{19}$ crystals, respectively, which compares favorably with the published X-ray densities of 5.11 gm/cc for $SrFe_{12}O_{19}$ [V. Adelsköld, Arkiv. Kemi., Min., Geol. 12A, 29 (1938)]and 5.28 gm/cc for $BaFe_{12}O_{19}$ [G. H. Jonker, H. P. J. Wijn, and P. B. Braun, Proc. Inst. Elco Engrs. (London) 104B, 249 (1957)]. A quantitative spectrochemical analysis shows that the crystals are 99.9+% pure with the main impurities being Al, Si, Ni, Mn, Mg, B, and Ca.

Electric magnets may also be cited as an example.

The plug structure 2, at least the leg portion 2″ of which is made of the magnet member illustrated above, preferably has an umbrella-shaped cap portion 2′ as shown in FIGS. 1 and 2. A plate-like cap may also be used. But the plug structure 2 having the umbrella-shaped cap portion 2′ is preferred since it has the advantage that it is useful for protecting the end portion of the opening of the artificial anus, and the area of contact between the cap and the skin surface is markedly decreased to thereby further reduce the feel of having a foreign object present by contact.

Figure 3:
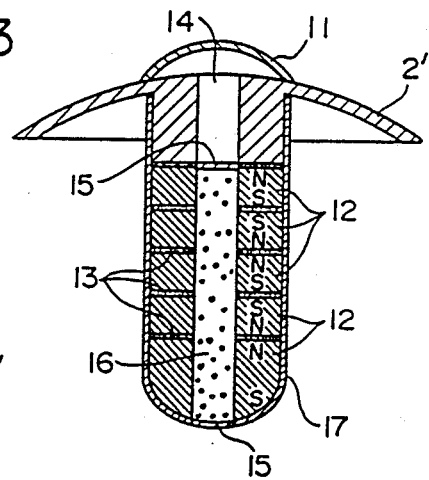
FIG. 3 is a longitudinal sectional view showing one example of the plug structure of the magnetic artificial anus of this invention.
Figure 4:
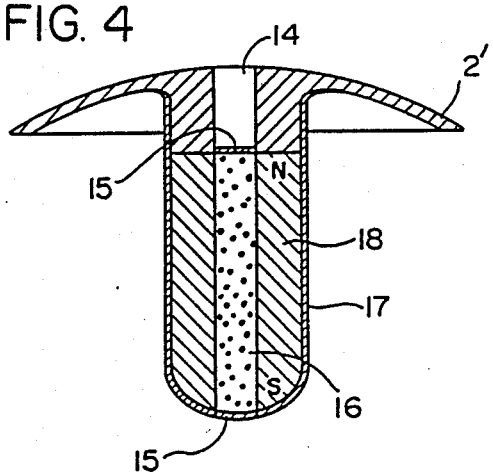
FIG. 4 is a similar longitudinal sectional view showing another example of the plug structure of the magnetic artificial anus of the present invention.
Figure 5:
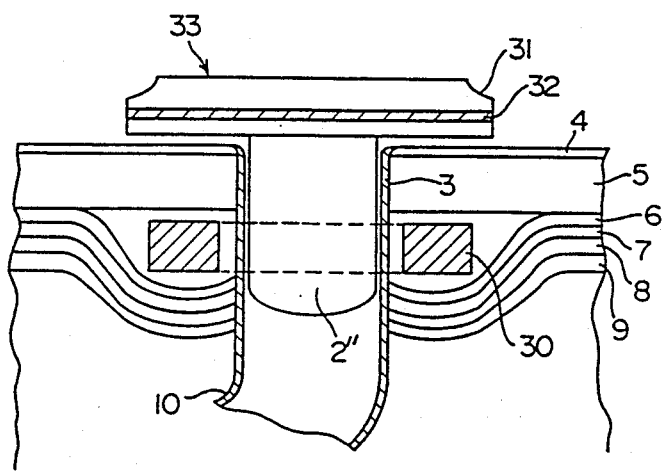
FIG. 5 is a longitudinal sectional view, similar to FIG. 1, showing one example of the conventional magnet-type artificial anus.

FIG. 3 shows one example of the plug structure having such an umbrella-shaped cap 2′, and FIG. 4, another example thereof. In the example of FIG. 3, a handle 11 is provided at the top part of the umbrella-shaped cap. In this example, the leg portion 2″ is formed of a hollow cylindrical body, and its end portion in the inserting direction is formed in a curved surface to permit easy insertion. Its outside diameter may be properly varied so as to conform to the inside diameter of the artificial anus wall 3, but is preferably slightly smaller than the inside diameter of the wall 3. Preferably, the length of the leg portion 2" is preset such that at the time of insertion, the end portion in the inserting direction terminates at a position slightly below the site of embedding the annular bag structure 1.

The leg portion 2" is formed of a magnet member, but it is not necessary to form the entire leg portion 2" from the magnet member. It is sufficient that at least that part of the leg portion which faces the annular bag structure 1 at the time of insertion is formed of the magnet member. In the example of FIG. 3, a plurality of ring-like permanent magnets 12 are stacked in the axial direction of the leg portion 2" via adhesive layers so that the same poles (for example, S/S, N/N) oppose each other. Furthermore, in this example, a ventilation hole 14 defined by the ring-like hollow portions of the ring-like permanent magnets has a gas permeating filter 15 both at an upper and a lower end. The space between the upper and lower end filters may be filled with a suitable gas-permeating filling material 16. The filling material may be an organic or inorganic fibrous filler, or an organic or inorganic filler in the form of a powder, granules, a porous body or another suitable shape. At this time, a filler having deodorizing ability, such as activated carbon or other various deodorants may be used as the filler, and this is preferred. The surface of the leg portion 2" is desirably formed of a film 17 obtained by coating a suitable coating material. The film can be formed of a bio-affinitive coating material. For example, in addition to materials similar to those illustrated above with regard to the bag structure 1, vinyl resins, olefinic resins, fluorine-containing resins, polyester resins, polyamide resins and other suitable film-forming resins may be utilized.

In the example of FIG. 4, an ordinary cylindrical permanent magnet 18 is used instead of the laminated composite magnet in FIG. 3, and the cap 2' is made of a magnetically permeable material such as wrought iron. Otherwise, the plug structure is the same as in FIG. 3.

The embodiments illustrated in FIGS. 3 and 4 are not limitative, and a magnet which can attract the magnetic fluid-filled annular bag structure 1 by a suitable magnetic attracting force can be properly selected and utilized.

Desirably, the combination of the magnetic fluid and the magnet is properly selected and changed so as to generate an attracting force which can withstand the inside pressure of the intestinal tube, for example about 20 to 50 cm $H_2O$.

EXAMPLE

Using four mature mongrel dogs, an artificial anus by the sigmoid colon was constructed at the left side abdominal portion, and at this time, a silicone rubber annular bag structure (inside diameter about 3 cm, outside diameter about 5 cm, wall thickness 0.1 mm) filled with about 20 ml of an aqueous sol of magnetic iron oxide-dextran complex (iron content: 400 mg/ml; dextran content: 210 mg/ml) was embedded between the outer fascia and the inner fascia of the abdominal wall.

The abdomen of one dog was incised. After the descending colon or the sigmoid colon was clystered, the descending colon portion was completely closed. Two catheters for injection of physiological saline and for inside pressure measurement were inserted between the closed portion and the artificial anus. A plug structure of the type shown in FIG. 3 (surface flux density 6,000 gauss) was inserted into the artificial anus. While physiological saline was injected from one catheter, the pressure of the inside of the intestinal tube was measured. No leakage of physiological saline was noted from the artificial anus to an intestnal tube inside pressure of up to 45 mm $H_2O$.

The same plug structure as described above was inserted into the artificial anus in each of the three remaining dogs. A chronic experiment was conducted by keeping them for 3 months while permitting bowel movement several times a day. In any of the dogs tested, no complication nor such troubles as pressing and necrosis or erosion of the artificial anus wall (the mucous membrane of the colon) were noted.

INDUSTRIAL UTILIZABILITY

As stated above, since the magnetic artificial anus in accordance with this invention can have a sphincter function, it is useful as an artificial anus for persons whose anuses have been cut and removed or who have otherwise lost a sphincter function.

I claim:
1. An implantable magnetic artificial anus having sphincter functions comprising:
   a flexible annular hollow bag formed of a bioaffinitive flexible film having a film thickness of 0.1 to 0.5 mm and filled with a magnetic fluid; and
   a plug member having in combination a cylindrical body defining upper and lower ends, and an umbrella shaped cap integral with the upper end thereof, said cylindrical body having permanent magnet disposed therein and said body having a hollow ventilation chamber extending from the upper to the lower end, said ventilation chamber having gas permeating filters disposed at each end thereof and said chamber being filled with gas permeating material, whereby said annular bag is disposed about the periphery of a natural or artificial colon and the cylindrical body of the plug member is inserted into the colon directly adjacent the annular bag such that the permanent magnet in the cylindrical body causing the flexible bag to constrict about said colon in a natural sphincter manner thereby securing the plug member within the colon.
2. The artificial anus set forth in claim 1 wherein the magnetic fluid is an aqueous sol of magnetic iron oxide-dextran complex.
3. The artificial anus set forth in claim 1 wherein the film has a film thickness of 0.1 to 0.2 mm.
4. The artificial anus set forth in claim 1 wherein the cylindrical body comprises a plurality of ring-like permanent magnets stacked in the axial direction of the cylindrical via adhesive layers so that the same poles of adjacent magnets oppose each other.
5. The artificial anus set forth in claim 1 wherein the cylindrical body comprises a single permanent magnet.

* * * * *